(12) United States Patent
Pison (10) Patent No.: US 9,943,292 B2
(45) Date of Patent: *Apr. 17, 2018

(54) BIOPSY INSTRUMENT FOR ENRICHING SAMPLE MATERIAL

(75) Inventor: Ulrich Pison, Berlin (DE)

(73) Assignee: OGENO GMBH, Berlin (DE)

( * ) Notice: Subject to any disclaimer, the term of this patent is extended or adjusted under 35 U.S.C. 154(b) by 1111 days.

This patent is subject to a terminal disclaimer.

(21) Appl. No.: 13/058,735

(22) PCT Filed: Sep. 8, 2009

(86) PCT No.: PCT/DE2009/001268
§ 371 (c)(1),
(2), (4) Date: May 10, 2011

(87) PCT Pub. No.: WO2010/025719
PCT Pub. Date: Mar. 11, 2010

(65) Prior Publication Data
US 2011/0213270 A1    Sep. 1, 2011

(30) Foreign Application Priority Data

Sep. 8, 2008   (DE) .................. 10 2008 046 635
Jun. 4, 2009   (DE) .................. 10 2009 024 134

(51) Int. Cl.
*A61B 10/02* (2006.01)
*A61B 10/00* (2006.01)
*A61B 10/04* (2006.01)

(52) U.S. Cl.
CPC .......... *A61B 10/02* (2013.01); *A61B 10/0045* (2013.01); *A61B 10/0064* (2013.01); *A61B 10/04* (2013.01); *A61B 2010/0077* (2013.01)

(58) Field of Classification Search
CPC ........ A61B 10/0045; A61B 2010/0077; A61B 10/02; A61B 10/04; A61B 10/0064
(Continued)

(56) References Cited

U.S. PATENT DOCUMENTS 4,817,631 A   4/1989 Schnepp-Pesch et al.
5,085,659 A * 2/1992 Rydell .................. A61B 10/04
                                               606/170
(Continued)

FOREIGN PATENT DOCUMENTS

CN   1767897 A   5/2006
EP   0263096 B1  4/1988
(Continued)

*Primary Examiner* — Sean Dougherty
*Assistant Examiner* — Patrick Fernandes
(74) *Attorney, Agent, or Firm* — Agris & Von Natzmer, LLP; Joyce Von Natzmer (57) ABSTRACT

The present invention relates to a biopsy instrument, comprising the following components: i. a guide element (1) comprising a spring-elastic distal (2) region and a proximal (3) region; ii. a biofunctionalized element (4) arranged between the distal and the proximal region of the guide element and whose surface has detection molecules, and iii. a stabilizing element (5) connected to the proximal region of the guide element. The invention further relates to the use of said biopsy instrument for enriching specific sample material from the body as well as to a biopsy kit and the use of the same for enriching specific sample material.

34 Claims, 4 Drawing Sheets

(58) Field of Classification Search
USPC .................................................. 600/562, 564
See application file for complete search history.

(56) References Cited

U.S. PATENT DOCUMENTS

| | | | |
|---|---|---|---|
| 5,273,051 A * | 12/1993 | Wilk | A61B 10/04 |
| | | | 600/562 |
| 5,282,476 A | 2/1994 | Terwilliger | |
| 5,961,534 A * | 10/1999 | Banik | A61B 10/06 |
| | | | 600/562 |
| 5,983,899 A | 11/1999 | Haellgren | |
| 6,659,996 B1 | 12/2003 | Kaldany | |
| 6,833,267 B1 * | 12/2004 | Kayyem | B82Y 15/00 |
| | | | 422/68.1 |
| 7,718,421 B2 | 5/2010 | Chen et al. | |
| 2002/0013539 A1 * | 1/2002 | Hung | A61B 10/0045 |
| | | | 600/573 |
| 2003/0049679 A1 | 3/2003 | Pompidou et al. | |
| 2003/0135153 A1 | 6/2003 | Hagemeier | |
| 2004/0077973 A1 * | 4/2004 | Groenke | A61B 10/025 |
| | | | 600/567 |
| 2004/0158275 A1 * | 8/2004 | Crank | A61F 2/013 |
| | | | 606/200 |
| 2006/0074443 A1 * | 4/2006 | Foerster et al. | 606/185 |
| 2006/0263799 A1 | 11/2006 | Dertinger et al. | |
| 2007/0003989 A1 | 1/2007 | Ellingsen et al. | |
| 2007/0016099 A1 * | 1/2007 | Chin | A61B 10/0275 |
| | | | 600/565 |
| 2007/0067882 A1 * | 3/2007 | Atanasoska | A61L 27/34 |
| | | | 606/192 |
| 2008/0213130 A1 | 9/2008 | Pison et al. | |
| 2009/0131274 A1 | 5/2009 | Pison et al. | |
| 2010/0168609 A1 | 7/2010 | Pison et al. | |
| 2011/0160296 A1 | 6/2011 | Pison et al. | |
| 2011/0213270 A1 | 9/2011 | Pison | |
| 2012/0302916 A1 | 11/2012 | Pison et al. | |
| 2013/0261373 A1 | 10/2013 | Pison et al. | |

FOREIGN PATENT DOCUMENTS

| | | |
|---|---|---|
| EP | 1779816 A2 | 5/2007 |
| JP | 2003510138 A | 3/2003 |
| WO | 98/22022 A1 | 5/1998 |
| WO | 01/23031 A1 | 4/2001 |
| WO | 2006050352 A1 | 5/2006 |
| WO | 2006131400 A1 | 12/2006 |
| WO | 2008/110392 A2 | 9/2008 |
| WO | 2009/147081 A1 | 12/2009 |

* cited by examiner

BIOPSY INSTRUMENT FOR ENRICHING SAMPLE MATERIAL

This is the U.S. national stage of International application PCT/DE2009/001268, filed Sep. 8, 2009 designating the United States and claims priority to German applications DE102008046635.2, filed Sep. 8, 2008 and DE102009024134.5, filed Jun. 4, 2009.

The present invention relates to a biopsy instrument for the enrichment of specific sample material and the use of the biopsy instrument for diagnosis, as well as a biopsy kit for the enrichment of cellular or molecular samples in various body cavity systems, such as a blood vessel, the spinal canal, the bile duct, or the lower urinary tract of humans or animals.

BACKGROUND OF THE INVENTION

In modern medicine, the biopsy, i.e., removal of material from a living human or animal body for examination by various methods such as microscopy, is carried out routinely. Typically, a method of this type is used for the diagnosis of premalignant and malignant cell transformations, which indicate the presence of cancerous or precancerous tumors. The routine techniques known as core biopsies, in the course of which complete tissue segments are taken for histological examination, make use of various types of hollow needle-like biopsy instruments. These instruments have needles with a sharp frontal edge or a notched stylet in order to cut into the tissue upon insertion into the selected area of the body. The tissue piece to be removed as a biopsy sample is taken up into the cylindrical bore of the cannula. When withdrawing the biopsy instrument from the body, the sample is retained in the cylindrical bore by mechanical means or by suction and is separated from the main body of the tissue during the withdrawal procedure. The samples typically have a generally elongated cylindrical shape or a longitudinal semi-cylindrical shape. The quality, e.g. the width, length and the proportion of crushed cells of biopsy samples for histological or cytological examination is an important factor that influences the study results. Tissue biopsy samples should reflect the structure of the living tissue as closely as possible. Accordingly, tension on the samples during excision and removal of tissue, as well as during removal from the cannula, should be avoided.

The removal of material from a living human or animal body for subsequent diagnostic procedures is usually done by obtaining a solid tissue sample by biopsy or by the removal of body fluids, e.g. in the form of a vascular puncture for obtaining a blood sample or by thoracentesis to obtain a pleural effusion, or joint aspiration for the production of synovial fluid, or by spinal canal puncture to obtain liquor, or generally by the puncture of a body cavity system for the extraction of material in liquid or liquid-like form. The present invention describes a biopsy instrument that allows, in a surprisingly simple manner, cellular or molecular samples in different cavity body systems of humans and animals to be enriched prior to removal, to ensure a sufficient concentration for downstream diagnostic procedures. Based on this biopsy instrument, corresponding technical instructions and guidelines that describe new or improved diagnostic procedures can be formulated.

U.S. Pat. No. 5,282,476 describes an automated device for the biopsy, in which the needle is attached to a stylet that guides the needle to the biopsy site. After insertion, the needle is driven out over the stylet, removing the sample with it. A means of suction is used to hold the sample in place. However, because of the means of suction, this biopsy instrument has a rather complex structure and requires considerable skill in handling. In the hands of an inexperienced user, the instrument can give uncertain results. It is also designed for the removal of material from solid body structures and not from body cavity systems.

In addition, instruments or sensors are known that serve to enrich the samples. WO/2006/131400 describes the use of a functionalism surface for the enrichment and recovery of molecules or isolated cells, such as from fetal trophoblasts in the maternal blood circulation. These are receptor structures anchored on the surface of the sensor, responding to specific cells or molecules in the bloodstream and, thus, permitting enrichment of this material in situ prior to physical removal from the body. However, to-date no embodiment of a biopsy instrument suitable for this task has been described that would allow manufacturing for use in humans and animals.

Furthermore, in the prior art, devices are described (for example, WO 01/23031 A1, EP 1779816 A2, US 2003/0135153, WO 98/22022 A1), with the aid of which certain drugs or dyes can be inserted into body cavities. Here, the active ingredients are introduced into the hollow sections of the devices and released upon reaching the target position. The disadvantage here is that the samples are obtained in a very inexact manner and the active ingredients are introduced into the devices in liquid form. In this way, the possible uses of the devices are limited.

The means described in the prior art for the removal or enrichment of samples cannot be used in all areas of the body. In particular, the endoscopic use of the described instruments/sensors is not possible or can only be performed with difficulty. Other major drawbacks are the precision with which the tissue area selected for the biopsy, and body cavity systems in particular, can be targeted with the instrument/sensor, the ease with which the instrument/sensor can be handled, injury caused to the patient by the procedure, as well as the cost of the instrument or sensor. In addition, no biopsy instrument is described that is designed for use in humans and animals to allow enrichment of the biopsy material in a low-risk way prior to removal of the samples from body cavity systems.

SUMMARY OF THE INVENTION

Based on this prior art, the object of the present invention is to provide a biopsy instrument that allows the specific enrichment of sample material by means of endoscopic equipment and from body cavity systems, as well as to allow subsequent diagnostic procedures during the dwell time in the body. An additional object of the invention is the development of a biopsy instrument that minimizes the risk of injury to the patient, especially since the dwell time of the biopsy instrument within the body for the diagnostic process is a new criterion for sample extraction.

Surprisingly, this task is solved by the features of the independent claims. Preferred embodiments of the invention emerge from the subsidiary claims.

It was a complete surprise that the inventive problem can be solved with a biopsy instrument comprised of the following components:
 i. a guide member comprised of a spring-elastic distal and a proximal portion,
 ii. a biofunction element that is attached between the distal and proximal portion of the guide element, the surface of which features detecting molecules, and iii. a stabilizing element connected with the proximal portion of the guide element.

The biopsy instrument is used for the enrichment of samples. This may be a sample from the group consisting of blood or blood plasma, lymph or chyle, urine, semen, vaginal secretions, amniotic fluid, saliva, gastric juice, bile, pancreatic juice, nasal secretions, bronchial secretions, alveolar fluid, cerebrospinal fluid, endolymph, aqueous humor, tears, synovial fluid, pleural fluid, pericardial fluid (pericardial liquor), peritoneal fluid, breast milk, sweat, menstrual fluid, or combinations thereof.

The biopsy instrument comprises at least one guide element, a biofunction element and a stabilizing element. The guide member has a distal and a proximal portion, whereby the distal portion is spring-elastic.

The terms "proximal" and "distal" refer to the person taking the biopsy sample. Accordingly, the proximal end of the biopsy instrument is the rear end that faces away from the patient.

The term "spring-elastic" describes the properties of a material which deforms under a load and when released regains its original shape. By this property, the distal portion of the guide member is well-secured, ensuring a low-to-non-existent risk of injury to the patient, because the spring-elastic portion deforms when it is in contact with a surface, such as a blood vessel wall or an organ, and thus the pressure on the surface is reduced.

A biofunction element is placed between the distal and proximal portion of the guide element. On its surface, the biofunction element has detection molecules, which are applied on its surface using chemical, electrochemical and/or biological processes. Detection molecules are also known to a person skilled in the art as capture molecules. These are molecules that preferentially interact with organic and inorganic materials. Polymers, for example, may be used as organic materials. About 90% of organic materials are composed of carbon, hydrogen and oxygen in varying proportions. The vast remainder of organic compounds can also contain nitrogen, sulphur, phosphorus and halogens. In addition, metal-organic materials, comprises a combination of metal and carbon, can also be used. Materials including types of glass, ceramics, hard materials, nano-structures and nano-crystals, silicon, and silicates can also be used as inorganic materials, i.e., those not substantially composed of carbon. Thus, due to the special configuration of the biofunction element, an enrichment of specific cells or molecules can take place in the body of humans and animals, that is, in situ, which is a departure from the usual technology and solves a long-standing problem of the prior art. Due to a high specificity of the biofunction element, a rapid enrichment of samples is achieved, treating patients gently and relieving them of stress.

In the proximal portion of the guide element is the stabilizing element, which can be firmly connected with the area or made more freely movable. The stabilizing element fixes the biofunction element during the biopsy, thus preventing dislocation of the biofunction element. Also, through the inventive embodiment of the biopsy instrument, removal of the instrument from the patient's body is guaranteed as an integral whole, i.e. the arrangement of the components prevents the dislocation of individual components, so that no component of the instrument remains in the patient's body.

The present inventive method describes a biopsy instrument that allows, in a surprisingly simple manner, cellular or molecular samples in different cavity body systems of humans and animals to be enriched prior to removal, to ensure a sufficient concentration for subsequent diagnostic procedures.

Advantages of the invented biopsy instrument are the accuracy with which the instrument can be positioned in the body area selected for the enrichment of samples, the specificity and sensitivity with which cells and molecules can be enriched in situ, and the ease with which the biopsy instrument can be handled. Also, the cost of the biopsy instrument is low. A fast and reliable enrichment of samples for analysis plays an important role in medicine and is an decisive criterion for the diagnosis of diseases.

The components of the biopsy instrument are preferentially arranged sequentially from distal to proximal, the biofunction element is arranged distally to the spring-elastic guide element, whereby the stabilizing element is located in the proximal portion of the guide element. This arrangement ensures that when inserting the biopsy instrument into the body, the spring-elastic region is distally arranged, thus minimizing the risk of injury to the patient. The biofunction element is still fixed by the proximal stabilizing element. Thus, a dislocation of the components is prevented during sample enrichment and loss of a component of the biopsy instrument is prevented. Moreover, the sequential arrangement of the components increases reliability and improves the efficiency of a biopsy. A knowledgeable person skilled in the art may be able to construct special forms of the biopsy instrument, in which two or more biofunction elements are arranged with different detection molecules between the distal and proximal portion of the guide element, or in which the fictionalization of the distal portion of the guide element takes place with detection molecules while preserving the spring-elastic material properties of this region.

It is also preferred that the distal portion of the biopsy instrument, i.e. the spring-elastic part of the guide element, be made of metallic or non-metallic materials. Accordingly, it can be manufactured in a preferred embodiment of stainless steel, but also of other metals. Metals indicate those chemical elements that, in contrast to the non-metals, are found in the periodic table to the left of the diagonal dividing line starting with the element beryllium (2nd group) through polonium (16th group), with their alloys and intermetallic compounds (including Laves phases, Heusler phases, Zintl phases, Hume-Rothery phases, NiTi, Co5, Nb3Sn and Ni3Al) with characteristic metallic properties. Metals include aluminum, beryllium, bismuth, lead, cadmium, chromium, iron, gallium, gold, indium, potassium, cobalt, copper, magnesium, manganese, molybdenum, sodium, nickel, osmium, palladium, platinum, mercury, rhodium, ruthenium, silver, tantalum, titanium, uranium, vanadium, tungsten, zinc, tin and zirconium. In an advantageous embodiment, an inner wire may be surrounded by an outer circular wire, so that the spring-elastic property is adjusted.

Alternatively, one can also use non-metallic materials from which thin cylindrical structures can be formed. For the purposes of the invention, a cylinder is an area delineated by two parallel, flat surfaces (base and top surface) and a jacket or cylinder surface, which is formed by parallel lines. Non-metals are gaseous (including hydrogen, nitrogen, oxygen, fluorine, chlorine or noble gases), liquid (including bromine) or solid (including boron, carbon, phosphorus, sulphur, iodine, or astatine) elements of a mostly electronegative character. Non-metals are found in the main groups (hydrogen in the 1st, the others in 13-18) of the periodic table.

Polymers can be used for non-metallic materials in a preferred embodiment. Polymers are taken to mean, pursuant to the definition of IUPAC ("The International Union of Pure and Applied Chemistry"), substances that are composed of a collective of chemical macromolecules (polymer molecules), which as a rule differ in terms of polymerization, molecular weight and chain length. In such so-called single polymer materials, so all macromolecules have the same structure and differ only in their chain length (polymerization). Such polymers can be described as a polymer homologue. Polymers can be selected from the group that consists of inorganic polymers, organometallic polymers, fully or partially aromatic polymers, homopolymers, copolymers, biopolymers, chemically modified polymers and/or synthetic polymers, and include polyethylene, polypropylene, polyvinyl chloride, polystyrene, polymethylmethacrylate, polyamide, polyester, polycarbonate, polyethylene terephthalate, polyethylene glycol, dendrimers, silicones, proteins, DNA, RNA, carbohydrates and polyhydroxxyalkanoate. Preferentially, polytetrafluoroethylene is used. The distal portion of the biopsy instrument manufactured from these materials represents a technical advance, because the risk of injury is reduced through the preferred embodiment. The material has spring-elastic properties, thus preventing injury to the surfaces that come into contact with the biopsy instrument.

Also advantageous is the fact that the stabilizing element of the biopsy instrument is essentially cylindrical. Due to the advantageous embodiment, the stabilizing element can be fitted easily to the proximal portion of the guide member by being pushed onto the proximal portion. Furthermore, the advantageous cylindrical shape achieves easy insertion and extraction of the biopsy instrument and thus increases efficiency.

It is also advantageous that the stabilizing element can slide over the proximal part of the guide element. The stabilizing element can be fit over the proximal portion of the guide element without there being a need to remove the additional components, mainly the biofunction element. The stabilizing element fixes the biofunction element, which is achieved through exact preparation of the component. Within the meaning of this invention, "exactly" means that at least two components are so made that they are compatible and fit exactly into the position anticipated for them. The ease with which the stabilizing element is applied to the proximal portion of the guide element facilitates the work of a person skilled in the art. Furthermore, the stabilizing element can be easily removed after a successful biopsy and enriched samples of the biofunction element prepared further or forwarded to the appropriate processing stations. The advantageous embodiment therefore represents serendipity because a single one has been selected from a number of possibilities, the result of which could not be predicted, so it constitutes patentable serendipity.

It is advantageously further anticipated that the outside diameter of the stabilizing element preferentially be equal to the outside diameter of the distal portion of the guide element. Thereby, a plane, i.e. a flat surface of the biopsy instrument, is formed, thus greatly reducing the risk of injury to the patient. Furthermore, through the advantageous embodiment, an easy insertion of the biopsy instrument into the regions of the body is guaranteed and ensures that it is removed in its entirety. On the whole, this means that the arrangement of the components prevents the dislocation of individual components, so that no component of the instrument remains in the patient's body.

A further advantageous embodiment includes a biopsy instrument, the stabilizing element of which is reversibly connected with the proximal portion of the guide element. Preferentially, in accordance with this embodiment, the stabilizing element can again be removed from the proximal portion of the guide element after the biopsy in order to release the biofunction element. The biofunction element can be dispatched to carry out downstream diagnostic procedures in the appropriate processing stations, or an analysis of the enriched samples can be done on site. The advantageous embodiment represents a technical advance, because a person skilled in the art can easily assemble and disassemble the biopsy instrument into the individual components after completion of sample enrichment. The stabilizing element can thus be used repeatedly, after appropriate disinfection, thereby reducing costs.

It is also advantageous if the stabilizing element is preferentially made of plastic. Plastics are taken to mean materials whose essential components comprise such macromolecular organic compounds as are created by modifying synthetic or natural products. In many cases, under certain conditions (heat and pressure), they are fusible and malleable. Plastics also include rubbers and chemical fibers. The synthetic raw materials for paints and adhesives can be counted among plastics. For the preferred embodiment, plastics from the group of modified natural materials, synthetic plastics (polycondensates, polymers, adduced polymers), thermosetting resins, and/or unsaturated polyester resins including cellulose nitrate, cellulose acetate, mixed cellulose esters, cellulose ethers, polyamide, polycarbonate, polyester, polyphenylene oxide, polysulphone, polyvinyl acetal, polyethylene, polypropylene, poly-1-butene, poly-4-methyl-1-pentene, ionomers, polyvinyl chloride, polyvinylidene chloride, polymethyl methacrylate, polyacrylonitrile, polystyrene, polyacetal, fluorine resins, polyvinyl alcohol, polyvinyl acetate, poly-p-xylylene, linear polyurethanes, chlorinated polyether, casein plastics, phenolic resin, urea resin, thiourea resin, melamine resin, epoxy resin, cross-linked polyurethanes, alkyd resin, allyl resin, silicone, polyimide, and/or polybenzimidazole may be used. Through the use of plastic in the design of the stabilizing element, biopsy instruments with rubber-elastic properties can be produced that can be placed at different biopsy sites in the body. Through the advantageous embodiment, increased reliability and flexibility in carrying out a biopsy can thus be achieved. Also, the risk of injury to the patient is dramatically reduced as the rubber-elastic embodiment does not injure any surfaces. Furthermore, by the use of plastics, costs for the configuration can be reduced.

It is advantageously anticipated that the stabilizing element and the proximal portion of the guide member are mechanically connected, bonded and/or welded. A stable connection of the proximal portion of the guide member and the stabilizing element is achieved, whereby the handling of the biopsy instrument is made easier for a person skilled in the art. By a mechanical connection, the connection can be made to be reversible, for which fasteners known to persons skilled in the art are used. Furthermore, a person skilled in the art knows of bonds or welds to ensure a secure and permanent connection of the proximal portion and the stabilizing element. The stable connection guarantees that the biopsy instrument can be introduced into a patient as an integral whole and also re-exported for sample enrichment, which improves reliability and simplifies the biopsy process itself.

Furthermore, it is advantageous that the guide element and the stabilizing element are made in a manufacturing process, which means that, for both components, materials can be used that are matched to the corresponding body parts in size and shape. An advantageous embodiment is plastic, modified from the group of natural products, synthetic plastics (polycondensates, polymers, adduced polymers), thermosetting resins, and/or unsaturated polyester resins, including cellulose nitrate, cellulose acetate, mixed cellulose esters, cellulose ethers, polyamide, polycarbonate, polyester, polyphenylene oxide, polysulphone, polyvinyl acetal, polyethylene, polypropylene, poly-1-butene, poly-4-methyl-1-pentene, ionomers, polyvinyl chloride, polyvinylidene chloride, polymethyl methacrylate, polyacrylonitrile, polystyrene, polyacetal, fluorine resins, polyvinyl alcohol, polyvinyl acetate, poly-p-xylylene, linear polyurethanes, chlorinated polyether, casein plastics, phenolic resin, urea resin, thiourea resin, melamine resin, epoxy resin, cross-linked polyurethanes, alkyd resin, allyl resin, silicone, polyimide, and/or polybenzimidazole. This can reduce the risk of injury to the patient because a flat surface of the instrument is formed. Even for a person skilled in the art, handling of the biopsy instrument is simplified, and manufacturing cost of the biopsy instrument can be kept low.

In an advantageous embodiment of the invention, the biofunction element has a substantially cylindrical shape, although other geometric shapes are used, including polygon, triangle, square, pentagon, hexagon, heptagon, octagon, nonagon, decagon, ellipse, circle, hyperbola, parabola, superellipse, spherical triangle, cycloid, rosette, helix, sphere, ellipsoid, ellipsoid of rotation, paraboloid of rotation, hyperboloid, oloid and polyhedron. With the embodiment, the biofunction element can be easily fitted from the proximal to the guide element, wherein it is fixed after being fitted to the area of the spring-elastic distal and proximal stabilizing element. Thus, dislocation of the biofunction element is not possible. Furthermore, the substantially cylindrical shape ensures that the biopsy instrument has a flat surface and easy insertion and extraction of the instrument can be guaranteed. Thus, through the advantageous embodiment, the quality of the sample enrichment can be increased while the time of sample enrichment is reduced.

Advantageously, the biofunction element has an outer diameter that is greater, equal to or smaller, preferentially 0.01 to 0.1 mm smaller, than the outside diameter of the distal portion of the guide element. Through the advantageous embodiment, it is achieved that the biofunction element can be fitted from the proximal to the guide element but is spatially limited by the distal portion. The outer diameter of the biofunction element is preferentially 0.01 to 0.1 mm smaller than the outside diameter of the distal portion of the guide element. By the preferred outer diameter of the biofunction element, a nearly flat surface of the biopsy instrument can be generated, by which, surprisingly, the optimum performance of the instrument is guaranteed, because during insertion and extraction of the biopsy instrument, the instrument does not interact with biological surfaces and so the positioning of the biopsy instrument is not adversely affected. The outside diameter of the biopsy instrument and, accordingly, the outside diameter of the biofunction element, are based on the anatomical structure in which the biopsy instrument is to be used. The length depends on the puncture site and positioning for sample collection in situ. The dimensions of the biopsy instrument can be adapted easily and quickly to the requirements of the different biopsy locations, resulting in a savings in time and costs.

It is also advantageously anticipated that the guide element between the distal and proximal portion has a receiver, which serves to receive the biofunction element. The receiver can be a recess in a variety of geometric shapes, including polygon, triangle, square, pentagon, hexagon, heptagon, octagon, nonagon, decagon, ellipse, circle, hyperbola, parabola, superellipse, spherical triangle, cycloid, rosette, helix, sphere, ellipsoid, ellipsoid of rotation, paraboloid, paraboloid of rotation, hyperboloid, oloid or polyhedron. An advantageous embodiment includes cylindrical, semicylindrical, clasp-like or foil-shaped recesses. These are examples that are not intended to limit the receiver. "Foil-shaped", as defined by the invention, is taken to mean that the receiver or the biofunction element are shaped so as to have a very small thickness and large area. The biofunction element is shaped according to the shape of the receiver. These alternative embodiments ensure that through the advantageous arrangement of a distally placed guide element followed by a biofunction element, a stabilizing element can be connected. Thus, it is ensured that, with minimal risk of injury to the patient, the biofunction of the instrument remains guaranteed and that after sample collection in situ the biopsy instrument can again be entirely removed from the body. Furthermore, due to the advantageous embodiment, the biopsy instrument can also be adjusted for different applications, whereby the amount of samples to be collected varies according to the shape of the receiver and of the biofunction element and can be adapted to the needs of the user.

Advantageously, the biofunction element includes metal, plastic, and/or ceramic materials. Metals include, as already stated above, aluminum, beryllium, bismuth, lead, cadmium, chromium, iron, gallium, gold, indium, potassium, cobalt, copper, magnesium, manganese, molybdenum, sodium, nickel, osmium, palladium, platinum, mercury, rhodium, ruthenium, silver, tantalum, titanium, uranium, vanadium, tungsten, zinc, tin, and zirconium. Ceramic materials are taken to mean a collective term for inorganic and predominantly non-metallic compounds or elements constructed of and containing more than 30% by volume of crystallized materials. Ceramic materials include alumina and kaolin, quartz, feldspar, lime, silimanite, magnesite, terracotta, majolica, faience, raku, paper clay or oxide ceramics. As an advantageous embodiment, plastics can also be used, as stated above, including cellulose nitrate, cellulose acetate, mixed cellulose esters, cellulose ethers, poly amide, polycarbonate, polyester, polyphenylene oxide, polysulfone, polyvinyl acetal, polyethylene, polypropylene, poly-1-butene, poly-4-methyl-1-pentene, ionomers, polyvinyl chloride, polyvinylidene chloride, polymethyl methacrylate, polyacrylonitrile, polystyrene, polyacetal, fluorine resins, polyvinyl alcohol, polyvinyl acetate, poly-p-xylylene, linear polyurethanes, chlorinated polyether, casein plastics, phenolic resin, urea resin, thiourea resin, melamine resin, epoxy resin, cross-linked polyurethanes, alkyd resin, allyl resin, silicone, polyimide, and/or polybenzimidazole. This advantageous embodiment ensures that effective and rapid sample preconcentration is achieved by the biofunction element and the collected material is bound to the biofunction element. The choice of material can also reduce the risk of injury to the patient. An increase in the surface of the materials is also possible to achieve increased effectiveness of the sample enrichment.

In a further advantageous embodiment of the invention, the detection molecules are preferentially selected from the group consisting of antibodies, antibody fragments, peptides, nucleic acids, receptors and/or inorganic materials. The application of detection molecules on the biofunction element reaches a specific enrichment of samples in situ prior to collection of the sample. The detection molecules can react with cells and/or molecules in the body of humans or animals and bind the cells and/or molecules. For this purpose, various detection molecules can be used and combined. Through specific positioning of the biopsy instrument in a desired location and through the specificity and sensitivity of the instrument, it can be achieved that even low concentrations of molecules and/or cells are detected by the detecting molecules. This represents a technical advance. Furthermore, it is possible, by varying the detection molecules, for the advantageous embodiment to find a wide scope of application. It may also be advantageous to apply various detection molecules to the biofunction element. For example, various detection molecules, such as those specific to a particular cell type, can be applied. This ensures that a specific sample is preferentially enriched. The molecules or cells are collected quickly and efficiently, and can then advantageously be quantified and analyzed in a laboratory. Particularly rapid and reliable sample enrichment plays a crucial role in medicine or, more precisely, the diagnosis of disease.

It is further advantageously anticipated that the biopsy instrument will also have a cover, whereby the cover preferentially has a sheath-shaped structure that covers the biofunction element. Other geometric shapes can be used, including a polygon, triangle, square, pentagon, hexagon, heptagon, octagon, nonagon, decagon, ellipse, circle, hyperbola, parabola, superellipse, spherical triangle, cycloid, rosette, helix, sphere, ellipsoid, ellipsoid of rotation, paraboloid, paraboloid of rotation, hyperboloid, oloid or polyhedron. This allows the biofunction element and sample material situated there after in situ enrichment to be protected from shearing or deformation before removal from the body and to avoid contamination outside the body. An advantageous embodiment is that the covering device is a sliding device that is pushed from the proximal portion of the biofunction element. However, other devices, including flap devices, are conceivable as a cover for the biofunction element. Through the advantageous embodiment, an enriched sample is protected, so measurement errors are reduced and the quality of the enrichment is improved.

It is advantageous that the covering preferentially cover the biofunction element, with the cover device including homopolymers, copolymers, biopolymers, chemically modified polymers and/or synthetic polymers. Suitable materials for the cover device are polymer materials, including polyethylene, polypropylene, polyvinyl chloride, polystyrene, polymethylmethacrylate, polyamide, polyester, polycarbonate, polyethylene terephthalate, polyethylene glycol, dendrimers, silicones, proteins, DNA, RNA, carbohydrates, and polyhydroxxyalkanoate. Preferentially polytetrafluoroethylene, however. In particular, if the adjacent components are manufactured from the same material, a good displacement of the individual components is achieved. Due to the advantageous embodiment, the cover device can be easily pushed over the biofunction element or cover it. Due to the advantageous embodiment, errors during biopsy taking are reduced, thus improving the efficiency and reducing the amount of work.

Another advantageous embodiment is that the biopsy instrument has a longitudinal bore for preferentially receiving a mandrain and/or other functional elements. The hole can be introduced into the biopsy instrument by methods known to those skilled in the art, and the width of the hole depends on the application and can vary accordingly. In the thin longitudinal bore channel, a mandrain (guide wire), for example, can be introduced and placed and advanced into the distal end of the biopsy instrument. Thus, the rigidity of the instrument for placement maneuvers in the body is optimized. Also, further fictionalizations, such as of an electronic nature, can be introduced to increase the usability of the biopsy instrument. The longitudinal bore improves safety and constitutes a simplification.

Moreover, configurations of the biopsy instrument are possible that include the following special cases but are not limited to them and which can be easily performed by a qualified person skilled in the art: a) the arrangement of two or more biofunction elements with different detection molecules between the distal and proximal section of the guide element, and b) fictionalization of the distal portion of the guide element to detect molecules while retaining the spring-elastic material properties of this region.

An additional object of the invention is to provide a biopsy kit for enrichment of samples from different regions of the body and body cavity systems and its application. The biopsy kit includes at least the following components of the biopsy instrument:

i. a guide element comprising a spring-elastic distal portion and a proximal portion,
 ii. one or more biofunction elements that are fitted between the distal and proximal portions of the guide element, on the surface of which the detecting molecules from at least one biofunction element have been applied, and
 iii. a stabilizing element connected with the proximal portion of the guide element.

The guide element, the biofunction element, and the stabilizing element are sequentially arranged from distal to proximal.

The biopsy kit includes at least one guide element, a biofunction element and a stabilizing element, whereby the guide element, the biofunction element and the stabilizing element are sequentially arranged from distal to proximal. The guide element has a distal and a proximal portion, whereby the distal portion is made to be spring-elastic. It can also be advantageous to construct special forms of the biopsy instrument, in which two or more biofunction elements with different detection molecules are arranged between the distal and proximal portion of the guide element. Advantageously, the fictionalization of the distal section of the guide element can occur with detection molecules and the spring-elastic material properties of this region can be retained. The biopsy kit can be supplemented with specific components that preferentially ease use for specific biopsy sites (such as blood vessels or in the urogenital apparatus) or allow use by means of other auxiliary medical devices (e.g., rigid or flexible endoscopes).

The terms "proximal" and "distal" refer to the person taking the biopsy sample. Accordingly, the proximal end of the biopsy instrument is the rear end that faces away from the patient.

The term "spring-elastic" describes the property of a material that deforms under a load and when released reacquires its original shape. The risk of injury to the patient from the biopsy is reduced by the biopsy kit, more precisely by the configuration of the biopsy kit. In particular, the spring-elastic distal portion of the guide element ensures that upon contact with a surface, such as a vessel wall or an organ, no damage to the biological material occurs. The spring-elastic guide member is deformed when the pressure is too great on the surface, thereby reducing the pressure on the surface.

A biofunction element is placed between the distal and proximal portion of the guide element. The biofunction element is used to accept the detection molecules that are deposited on its surface. Detection molecules are molecules that interact with organic and inorganic materials. Thus, due to the special configuration of the biofunction element, an enrichment of specific cells or molecules can take place in the body of humans and animals, that is, in situ, which is a departure from the usual technology and solves a long-standing problem of the prior art. Due to a high specificity of the biofunction element, a rapid enrichment of sample material is achieved, which is gentle and relieves the patient of stress.

Furthermore, a stabilizing element is connected with the proximal portion of the guide element. The stabilizing element is used to fix the biofunction element during the biopsy, thus preventing dislocation of the biofunction element. Thus, it is achieved that the biopsy instrument is removed from the patient in its entirety, i.e. no components of the biopsy instrument interact with surfaces in such a way as to damage the surfaces and no components of the instrument remain in regions of the body. Advantages of the inventive biopsy kit are the accuracy with which the instrument can be positioned in body regions and the specificity and sensitivity with which cells and molecules can be enriched in situ. The biopsy kit is easily operated by a person skilled in the art and reduces the risk of injury to the patient. Other advantages are the low cost of the biopsy kit and a high degree of flexibility in the design for different biopsy sites and applications, also using auxiliary tools such as endoscopes. In addition, a fast and reliable enrichment of samples for analysis plays an important role in the diagnosis of diseases.

A biopsy kit is provided with which it is possible to position the components necessary for sample enrichment, to keep them stationary for the amount of time needed for keeping the specific sample material in the body and remove them entirely together with the collected sample material after the dwell time. For proper positioning for sample collection and for the successful removal procedure of the sample material from the body, there are visual or other guide markings on the components of the biopsy kit which may be realized through engraving, color, or tactile or signaling marks and which allow determination of a geographical location of the biopsy instrument during sample collection and positioning within the body, and for the process of removing the biopsy instrument from the body. The positioning of the biopsy instrument can be ensured in situ by imaging techniques. For this purpose, pacifying vectors known to a person skilled in the art are to be used from the construction side. Also, the biopsy kit can be adapted for specific biopsy sites with regard to the dimensions of the individual components and supplemented with auxiliary tools to make components that are necessary or desirable for special applications available during the biopsy. Furthermore, the biopsy kit can be provided as a single-use item, which better meets the hygiene standards in medical facilities.

The biopsy kit may be advantageously used to remove samples, preferentially from the blood vascular system, including the ventricles, the pulmonary and systemic circulation and the arterial and venous system as special biopsy sites, the gastrointestinal tract; the biopsy instrument can be selectively positioned from the oral or anal direction, from the efferent glandular ducts of the pancreas, lachrymal gland, parotid gland, from the efferent ducts of the mucosal glands, mixed glands, and skin and sweat glands including the mammary gland, from the spinal canal or brain-chamber system, from the gall bladder and its efferent anatomical structures, from the efferent urinary tract or the lymphatic system, or to be used to take samples from the body cavities of the abdomen or the chest, the uterus, the urogenital apparatus, or a joint space.

A flexible design of the biopsy kit allows the enrichment of samples in different systems. Thus, the biofunction element can be equipped with different detection molecules in accordance with the requirements, so as to allow the detection of system-specific samples. One preferred use is the vascular system of the body. In this case, the biopsy kit is positioned in the vascular system through a vascular indwelling cannula. Further areas of application include the gastrointestinal tract, the efferent bile ducts, the pancreatic duct, and the urinary tract. While being used in the cardiovascular system, the outside diameter of the biopsy kit is oriented to the diameter of the blood vessel, with the length dependent on the puncture site and positioning for sample collection in situ. The outer diameter can be adjusted accordingly for placement in the pancreatic duct, common bile duct, cystic duct, or the urinary tract, or the bladder or the peritoneum or the tracheobronchial tree, or the pleural cavity or joint space. The advantageous embodiment and dimensioning can thus be undertaken through quick and simple adaptations by a person skilled in the art. Accordingly, it solves a long-standing problem in the prior art and makes available a fast and specific embodiment that can preferentially be used in body cavity systems in different regions of the body.

Descriptions of biopsy kit embodiments are made, for example, in the case of applications using an endoscope and for enrichment and taking of samples from the vascular system as the main case of application, the composition of the biopsy kit is not limited to these individual cases but can be changed or supplemented for other applications by a qualified person skilled in the art.

The use of a biopsy kit is advantageous if the biopsy instrument is placed with the aid of auxiliary endoscopic tools, preferentially a gastroduodenoscope, cystoscope, urteroscope, sigmoidoscope, proctoscope, coloscope, arthroscope, laparoscope, colposcope, hysteroscope, ophthalmoscope, laryngoscope, and/or bronchoscope. As defined by the invention, an endoscope is a device with which the interior of live or dead organisms can be examined or manipulated. To use the biopsy instrument through an endoscope, the following elements are advantageous as components of the biopsy kit:

i. a guide element comprising a spring-elastic distal and a proximal portion,
ii. a biofunction element with detection molecules, which is placed between the distal and proximal portion of the guide element,
iii. a stabilizing element connected with the proximal portion of the guide element,
iv. an adapter that allows insertion of the biopsy instrument through the working channel of the endoscope, and
v. a transparent and sliding sheath that can be attached to the adapter, to surround the biopsy instrument when outside the body and ensure hygienic handling during its dwell time in the body.

The length of the entire biopsy kit, including the guide element, the biofunction element, and the stabilizing element, is to be selected in such a manner that the endoscope can be removed from the body after endoscopic placement, usually via the instrument channel of the endoscope, without changing the position of the biopsy kit. This can be achieved by adapting the total length of the biopsy kit to the total length of the endoscope. A knowledgeable person skilled in the art may be able to construct special forms of the biopsy instrument in which two or more biofunction elements are arranged with different detection molecules between the distal and proximal portion of the guide element, or in which the fictionalization of the distal section of the guide element takes place with detection molecules while preserving the spring-elastic material properties this region.

The use of a biopsy kit is advantageous if the biopsy instrument is inserted into a vascular system through vascular access. Here, the detection molecules applied to the biofunction element can detect different molecules and/or cells in the vascular system. For the use of biopsy kits with vascular access, the following components are useful as additional components of the biopsy kit:

i. an indwelling vascular cannula with puncture needle;
ii. an adapter that is attached to indwelling vascular cannula and can be positioned intravascularly using the biopsy instrument;
iii. a port that is preferentially configured to be located on the adapter and through which an infusion solution can be applied during the dwell time of the biopsy instrument in the body;
iv. a transparent and sliding sheath that can be attached to the adapter, to surround the biopsy instrument when outside the body and ensure hygienic handling during its dwell time in the body.

Through the advantageous embodiment, sample enrichment with a high yield can be achieved quickly and efficiently when the biopsy kit is inserted into a vascular system via vascular access. The collected sample can be analyzed directly after extraction from the vascular system or can be forwarded to the appropriate processing stations. The embodiment thus represents a significant lightening of the workload for hospital staff.

In a very similar way, the biopsy kit for enrichment and collection of test material from the spinal canal and the epidural space can be used if instead of the indwelling vascular cannula a spinal puncture cannula or cannula for puncture of the epidural space is used as, for example, in epidural anesthesia.

In addition to placement via vascular cannula and via endoscope, placement as part of an operation or in a minimally invasive surgical operation is advantageous, which, with respect to the demands of the dimensions of the biopsy instrument, advantageously establishes no additional requirements other than those already stated. The advantageous embodiment leads to an improvement in the quality and increase in the reliability of sample enrichment.

It is preferred that the biopsy instrument and/or the kit for enrichment of samples be used and that the samples are preferentially used for diagnosis, in particular prenatal diagnosis, cancer diagnosis, treatment, follow-up (point-of-care diagnostics) and/or for the diagnosis of homoeostasis in patients. Furthermore, the biopsy instrument can be advantageously used to diagnose a disease selected from the group consisting of inherited diseases, proliferative diseases, inflammatory diseases, autoimmune diseases, infectious diseases, hormonal disorders, diseases of blood and blood-forming organs, diseases of the digestive tract, liver, bile, the pancreas, diseases of the urogenital tract and kidney, diseases of the heart, abnormal changes in blood vessel system and lymphatic system disorders, pulmonary conditions, diseases of the central or peripheral nervous system and electrical stimulus transmission and neurodegenerative diseases. The biopsy instrument advantageously collects samples that can be used to diagnose these diseases, that is, the biopsy instrument is used to generate an intermediate step. The biopsy instrument can thus be used for diagnosis of different diseases.

Preferred hereditary diseases include, for example, autosomal recessive, autosomal dominant, and mitochondrial gonosomal or extrachromosomal hereditary disease and/or any disease that can be traced to a genetic predisposition. Proliferative diseases include tumors, preferentially precancerous, dysplasia, neuroendocrine tumors, endometriosis and/or metaplasia.

Preferred autoimmune diseases include rheumatoid arthritis, inflammatory bowel disease, osteoarthritis, neuropathic pain, alopecia areata, psoriasis, psoriatic arthritis, acute pancreatitis, allograft rejection, allergies, allergic inflammation of the lung, multiple sclerosis, Alzheimer's disease, Crohn's disease and/or systemic lupus erythematous.

Infectious diseases include, preferentially, infections caused by parasitic disease, bacterial disease and/or viral diseases.

Preferred hormonal disorders include disorders of sugar metabolism, lipid metabolism, protein metabolism, sexual development and reproduction, water-salt balance, growth and/or cell formation.

The biopsy instrument comprises a distal spring-elastic guide element and a proximal stabilizing element, wherein one or more biofunction elements are fitted between the distal and proximal portion. On the surface of at least one biofunction element are detection molecules, including applied antibodies, nucleic acid or other capture structures known to a person skilled in the art. It is advantageous to construct special forms of the biopsy instrument, in which two or more biofunction elements are arranged with different detection molecules between the distal and proximal portion of the guide element, or in which the fictionalization of the distal section of the guide element is undertaken with detection molecules while preserving the spring-elastic material properties of this region. The proximal stabilizing element is used to stabilize the biofunction element and prevent its dislocation during insertion and extraction of the biopsy instrument. The spring-elastic portion of the guide element prevents injury to biological surfaces when inserting the biopsy instrument into a region of the body. Detection molecules are applied on the biofunction element, where they interact with organic and/or inorganic materials. Depending on the biopsy sites, the biofunction element can be equipped with specific detection molecules in order to enrich defined samples. The dwell time of the biopsy instrument in the body can vary and is dependent on the present concentrations of the material to be enriched. The biopsy instrument can be positioned in the body so that a specific enrichment is possible. Furthermore, such a combination of detection molecules is possible that enrichment of different samples is achieved. This represents a step forward, since rapid and reliable diagnosis and treatment follow-up are possible. After successful enrichment of the sample, the biofunction element is covered by a covering device, preventing loss of the sample during removal from the body and contamination outside the body. By using the biopsy instrument, sampling errors can be prevented and high specificity ensured. Furthermore, it can be used for the enrichment of samples that are present in low concentrations in remote regions of the body.

Due to the simple and quick replacement of the detection molecules of the biofunction element or the biofunction element itself, the biopsy instrument can be used for diagnosis in various medical fields. In prenatal and tumor diagnosis especially, rapid and reliable diagnosis is crucial.

When detected early, diseases such as heart defects, spina bifida and cleft lip and palate can be treated. Thus, use of the biopsy instrument with the appropriate detection molecules offers the possibility to enrich samples and analyze them for diseases and to monitor, examine and change the effect of a chosen therapy if necessary. In the field of cancer diagnosis as well, rapid and reliable detection is essential in order to start, monitor, and, if necessary, adjust therapeutic treatments promptly. This requires, however, that the tumor be identified. The use of the biopsy instrument opens up the possibility of cancer markers that are characteristic of certain types of tumors to be enriched in a region of the body, such as the vascular system or efferent glandular ducts, thus enabling quick diagnosis and checking of the therapy course.

Advantageously, the biopsy instrument can be used for monitoring the therapy course, which means that samples can be collected with the biopsy instrument, analyzed, and used to check the course of therapy. This includes the monitoring of tumor treatment, monitoring of an autologous, syngeneic, allogeneic, xenogeneic or alloplastic transplant, monitoring of an inflammatory disease, monitoring of infectious disease, monitoring of a hormonal disorder, monitoring of a psychiatric disorder and/or monitoring of a neurodegenerative disease. Surprisingly, the biopsy instrument can be easily and reliably adapted to the diagnosis of various diseases by one or more biofunction elements being provided with capture structures. A person skilled in the art is familiar with these capture structures, which also preferentially automates the analysis of the collected samples. The samples are, therefore, evaluated within a short time and the collected data can be advantageously used to decide on further treatment.

Particularly advantageously, the instrument can be used for primary diagnosis, the diagnosis of tumor spread, or tumor grading. It can advantageously be taken from at-risk patients in order to take samples over a longer period and at regular intervals of time, thus potentially detecting origination of a tumor at an early stage. For example, the collected biopsy samples are analyzed and evaluated by a laboratory. However, the instrument can be used not only for primary diagnosis but also for long-term monitoring of tumor spread. For example, the tumor growth or metastasis of a tumor can be monitored. These data in conjunction with, for example, the degree of differentiation (tumor grading) of the tumor advantageously give the treating physician important information that may be crucial for the further course of treatment. Advantageously, the collected samples will be analyzed quickly and reliably, which is essential for successful treatment.

Advantageously, the biopsy instrument can be used for prenatal diagnosis. Here, samples are collected and preferentially tested for gene mutations, chromosome mutations and chromosomal aberrations from the group consisting of deletion, inversion, duplication, translocation, ring chromosomes, and/or a failure of gene transcription, gene translation, mRNA stability, splicing variants, a disorder of mRNA transport into the cytoplasm, protein biosynthesis and/or epigenetic factors. It can advantageously detect molecules called capture molecules that are applied to the surface of one or more biofunction elements. The molecules are preferentially specific to the sample to be detected. The collected samples may, for example, be further analyzed in a lab and be sent to a treating physician. Advantageously, through the enrichment of preferentially exclusively specific samples, the analysis is substantially simplified and can be performed in less time. The biopsy instrument not only allows faster analysis but also improves the quality of the samples. Preferentially, specific samples are collected, which are advantageously protected by extracting the instrument from the body before a dislocation.

Furthermore, the biopsy instrument can be used to monitor the homoeostasis of patients. Especially with serious illnesses or instrument-based surgical procedures, continuous monitoring of the patient's condition is required. The biopsy instrument can be used universally for this purpose and advantageously adapted to the different requirements easily, quickly and inexpensively.

Further advantageous measures are described in the remaining subsidiary claims.

The invention will now be described with reference to figures showing examples, but is not limited to these. Illustrations.

BRIEF DESCRIPTION OF THE DRAWINGS

DETAILED DESCRIPTION OF THE DRAWINGS

Figure 1:
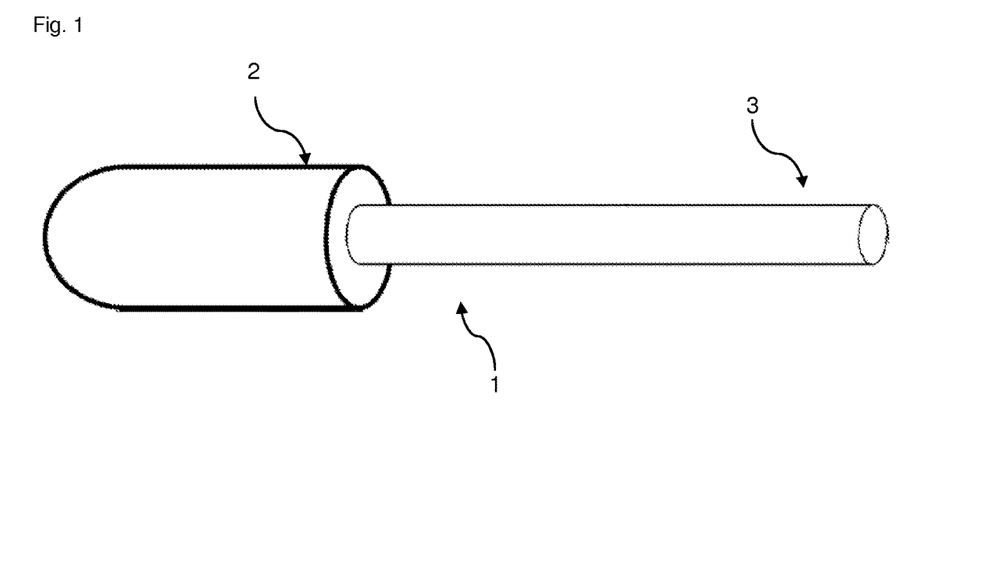
FIG. 1 a side view of a guide element with a distal and proximal portion.

FIG. 1 shows a schematic side view of a guide element. The guide member 1 comprises a distal 2 and proximal 3 portion. The distal portion 2 of the guide element 1 is designed to be spring-elastic. Preferentially, it can be manufactured of metals. Alternatively, one can also use non-metallic materials from which thin cylindrical structures can be formed. Polymer materials such as polytetrafluoroethylene may be considered for this. The distal portion 2 of the guide element 1 is firmly connected to the proximal portion 3. The distal 2 and proximal 3 portion of the guide element 1 can also be produced in a manufacturing process where the material allows, for example, this is possible by using suitable plastic materials for the production.

Figure 2:
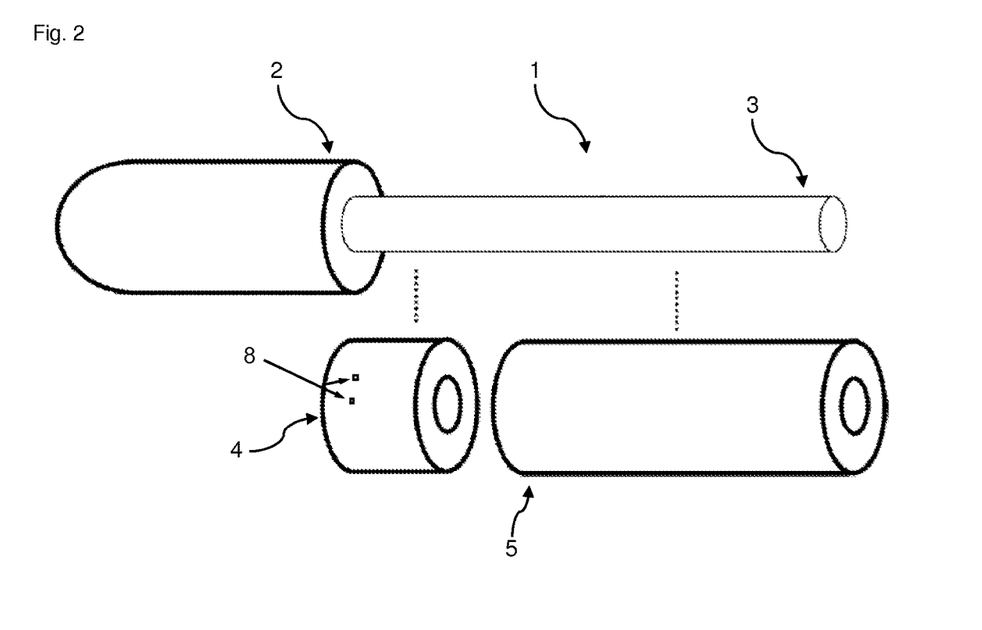
FIG. 2 a side view of a guide element with a cylindrical biofunction element and a cylindrical stabilizing element, FIG. 3 a side view of a biopsy instrument with a receiver for a semi-cylindrical biofunction element, FIG. 4 a side view of a biopsy instrument, with a receiver for two semi-cylindrical biofunction elements, FIG. 5 a side view of a biopsy instrument with a webbed receiver for a clamp-shaped, semi-cylindrical biofunction element, FIG. 6 a side view of a biopsy instrument with a receiver for a foil-shaped biofunction element, FIG. 7 a side view of a biopsy instrument with a covering device, and FIG. 8 a side view of a biopsy instrument with a covering device over a biofunction element.

In FIG. 2 a schematic side view of a guide element with a biofunction element and a stabilizing element is shown. The biofunction element 4 in FIG. 2 can carry detection molecules 8 on its surface that react with specific cells and/or molecules in the body of humans and animals and, thus, permit an enrichment of samples in situ prior to removal from the body. The design of this element is essentially executed as a cylindrical hollow body that in terms of its size is dimensioned so that it can be fitted from the proximal portion 3 to the guide element 1. To this end, the inner diameter of this component is greater than the outer diameter of the proximal portion 3 of the guide element 1. The outer diameter of the biofunction element 4 may be greater, equal or smaller in relation to the distal portion 2 of the guide element 1. The outer diameter of the biofunction element 4 is preferentially 0.01 to 0.1 mm smaller than the outside diameter of the distal portion 2 of the guide element 1. Materials for the production of this component include metals, plastics or ceramic materials that can serve as a substrate for anchoring of detection molecules. An embodiment in the form of tiny hollow fibers and sponges is also possible.

Furthermore, FIG. 2 shows a stabilizing element 5. This component is characterized in that it is tubular and can fit exactly over the proximal portion 3 of the guide element 1. The outer diameter of the stabilizer element 5 corresponds to the outer diameter of the distal portion 2 of the guide element 1 The wall thickness of this tubular member is sized so that the biofunction element 4 is fixed to slip freely through the stabilizing element 5 on the guide element 1. To that end, the stabilizing element 5 and the proximal portion 3 of the guide member 1 can enter into a stable combination, which can be achieved, without loss of function, through e.g., mechanical bonding or by welding these elements at the proximal end of the biopsy instrument. It is also advantageous if the two components are connected to each other reversibly. Thus, it can be ensured that the biofunction element samples can be removed from the biopsy instrument after successful enrichment and sent to the appropriate laboratories for subsequent diagnostic procedures to be performed. Through the use of materials for the stabilizing element, which give its rubber-elastic properties, biopsy instruments can be manufactured that can be placed optimally at different biopsy sites in the body.

A variant of the biopsy instrument comprises the biofunction element 4 in FIG. 2 not only in singular form, but in a double or multiple version, each equipped with different detection molecules applied behind one another on the proximal portion 3 of the guide element 1, followed by the stabilizing element 5.

Figure 3:
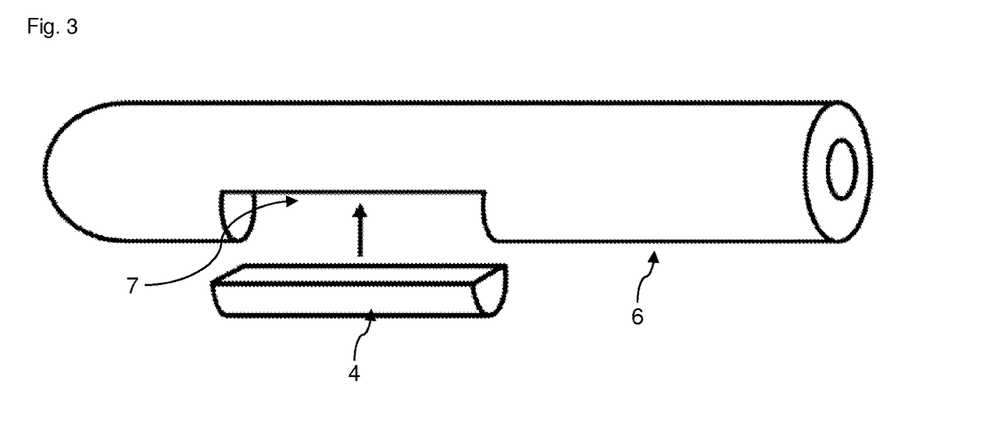

FIG. 3. shows a side view of a biopsy instrument, with a receiver for a semi-cylindrical biofunction element. The guide member 1 and the stabilizing element 5 can be machined in a manufacturing process and accordingly be permanently connected. The guide member/stabilizing element 6 manufactured in this way has a receiver 7, which serves to receive a biofunction element 4. The shape of the receiver 7 can have different forms, such as the shape of a half-cylinder. The biofunction element 4 is shaped according to the receiver 7. This allows the variation of the samples to be collected, or a quick and easy exchange of biofunction element 4 in order to adapt it to new situations.

Figure 4:
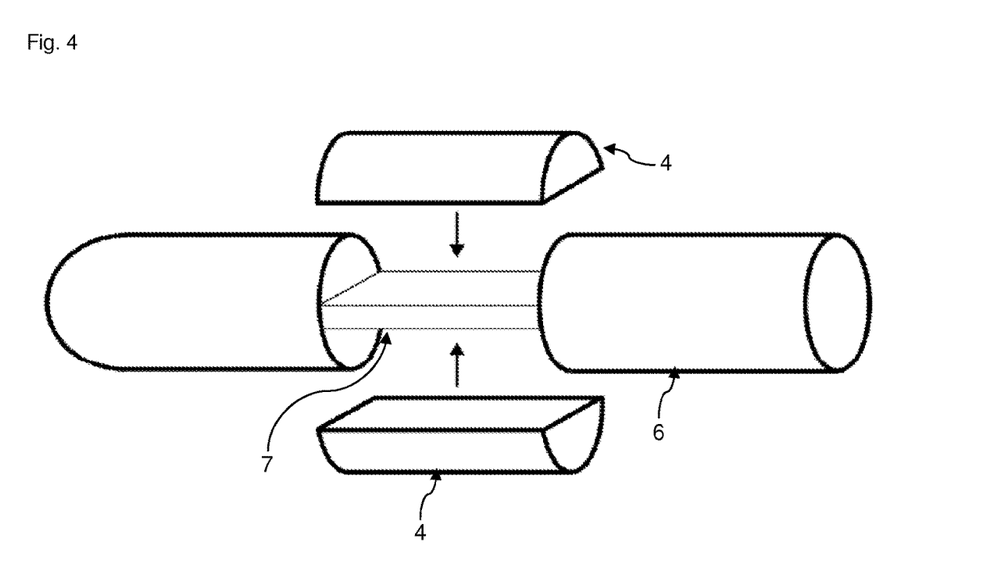

FIG. 4 shows a side view of a biopsy instrument, with a receiver for two semi-cylindrical biofunction elements. The biopsy instrument can be designed so that the guide member 1 and the stabilizing element 5 in FIG. 2 can be fabricated in a manufacturing process, yielding a guide element/stabilization element 6, and a receiver 7 can thus be inserted into the two biofunction elements 4. Here, the receiver 7 can be shaped such that two semi-cylindrical biofunction elements 4 can be inserted into these. Different detection molecules can be fitted to the two biofunction elements 4, thus allowing the enrichment of different cells and/or molecules. Moreover, with such a form factor, the yield of the sample is increased.

Figure 5:
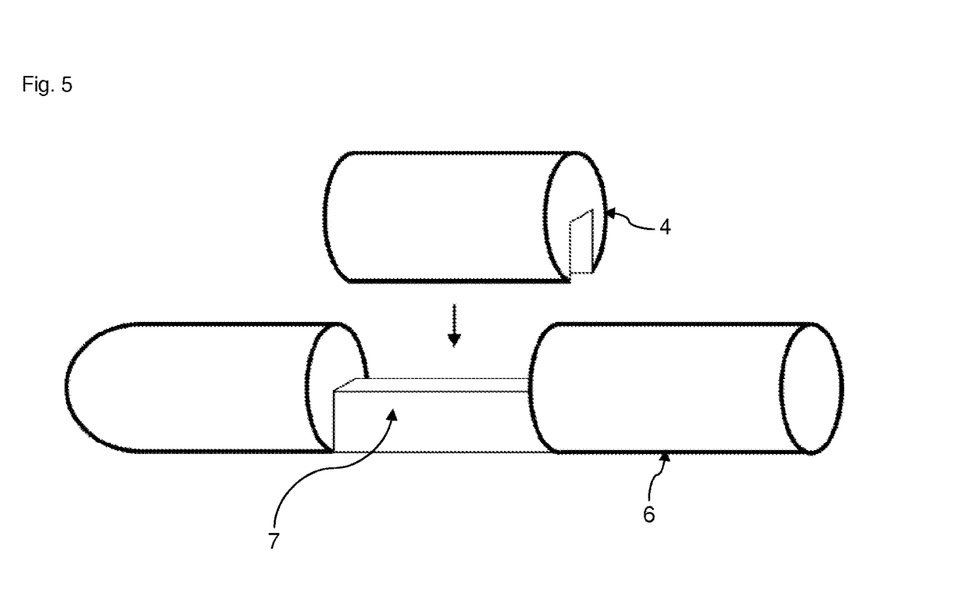

FIG. 5 shows a side view of a biopsy instrument, with a webbed receiver for a clamp-shaped semi-cylindrical biofunction element. The receiver 7 can be configured so that it is webbed and, therefore, accepts a clasp-shaped biofunction element 4. The biofunction element 4 designed in this way can be replaced quickly. In this design variant, a biofunction element 4 is arranged between a distal portion 2 and a proximal stabilizing element 5. Thus, it is ensured that with minimal risk of injury to the patient the biofunction of the instrument remains guaranteed and, after sample collection in situ, that the biopsy instrument can again be entirely removed from the body from the outside.

Figure 6:
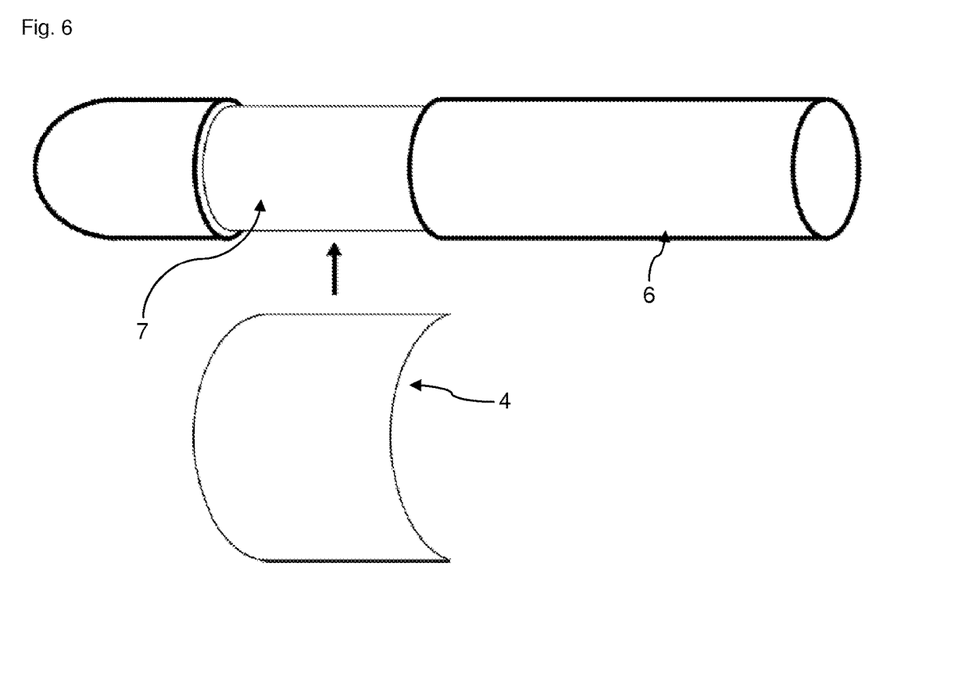

In FIG. 6 a side view of a biopsy instrument, with a receiver for a foil-shaped biofunction element is shown. For applications that require the reduction of the external diameter of the biopsy instrument, a foil-shaped receiver 7 is used for receiving a foil-shaped biofunction element 4. A film-shaped biofunction element is taken to mean for the purposes of this invention a shape with a very small thickness and large area. This embodiment can particularly be used in small blood vessels, in which samples must be enriched. Even specific detection molecules in the form of an inorganic material with which the enrichment of certain organic and/or inorganic molecules can be achieved can be inserted into the receiver 7. Thus, the biopsy instrument can be used for the enrichment of cells and/or molecules present in low concentrations in the regions of the body.

Figure 7:
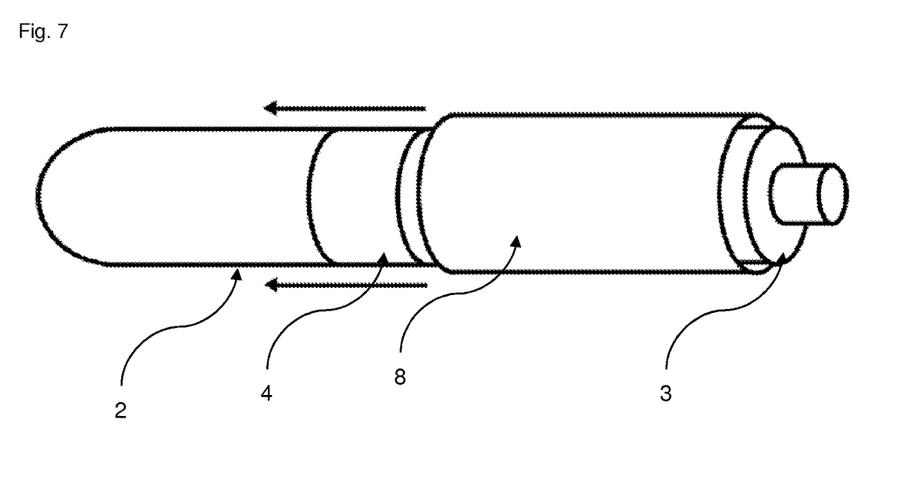

FIG. 7 shows a side view of a biopsy instrument with a covering device. Here, a covering device 8 that may include a sheath-shaped structure and which slides on the biopsy instrument is shown. This covering device 8 is fitted from the proximal portion of the guide element to the biopsy instrument. Polymers, preferentially polytetrafluoroethylene, are suitable materials for the covering device 8. In particular, if the adjacent components are manufactured from the same material, a good displacement of the individual components is achieved.

Figure 8:
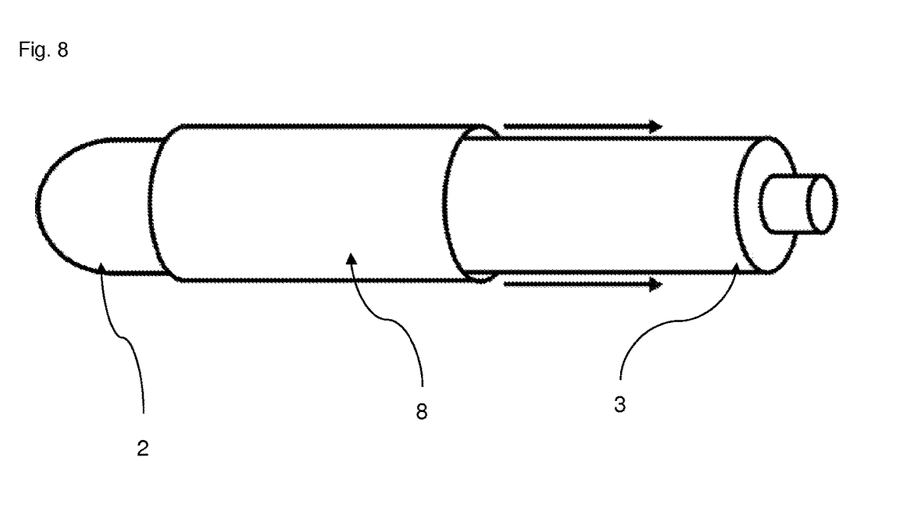

FIG. 8 depicts a side view of a biopsy instrument with a covering device over a biofunction element. Here, the covering 8 is applied to the guide element/stabilizing element 6 and serves to cover the biofunction element 4. After enrichment of the samples, the cover device is pushed in the distal direction of the biofunction element 4, whereby the biofunction element 4 and the enriched sample material are protected during extraction from the body regions and contamination is avoided. Thus, high quality and yield can be achieved.

It is understood that the present invention can be implemented through numerous other alternative embodiments and the advantages mentioned above are not limited to any embodiment. The following claims are intended to define the scope of the invention and include the claimed devices and applications and their equivalents.

REFERENCE LIST

1 Guide element
2 Distal portion
3 Proximal portion
4 Biofunction element
5 Stabilizing element
6 Guide element/stabilization element
7 Receiver
8 Covering device

The invention claimed is:

1. A biopsy instrument for enrichment of sample material, comprising,
   i. a guide element comprising a spring-elastic distal portion at a tip of the guide element which is configured so that no injury occurs to surfaces that come in contact with the biopsy instrument, and a proximal portion,
   ii. a biofunction element that is fitted between the spring elastic distal and proximal portions of the guide element, with a surface which comprises capture molecules which are configured to enrich the sample material, molecules or a combination of cells and molecules in a body of a human or an animal, wherein the biofunction element has an outer diameter that is equal to or smaller than the outside diameter of the spring elastic distal portion of the guide element and/or wherein the outer diameter of the biofunction element is 0.01 to 0.1 mm smaller than the outside diameter of the distal portion of the guide element, and iii. a stabilizing element connected with the proximal portion of the guide element and directly abutting the biofunction element, wherein the stabilizing element is configured to be slid over the proximal portion of the guide element and wherein the biofunctional element is configured to slip freely through the stabilizing element.

2. The biopsy instrument according to claim 1, wherein the components are sequentially arranged from distally to proximally.

3. The biopsy instrument according to claim 1, wherein the spring elastic distal portion is non-metallic.

4. The biopsy instrument according to claim 1, wherein the stabilizing element is cylindrical.

5. The biopsy instrument according to claim 1, wherein an outer diameter of the stabilizing element and an outer diameter of the distal portion of the guide element are equal.

6. The biopsy instrument according to claim 1, wherein the stabilizing element is reversibly connected to the proximal portion of the guide element.

7. The biopsy instrument according to claim 1, wherein the stabilizing element is made of plastic.

8. The biopsy instrument according to claim 1, wherein the stabilizing element is mechanically connected, bonded and/or welded to the proximal portion of the guide element.

9. The biopsy instrument according to claim 1, wherein the biofunction element has a cylindrical shape.

10. The biopsy instrument according to claim 1, wherein the biofunction element has an outer diameter that is equal to or smaller than the outside diameter of the spring elastic distal portion of the guide element.

11. The biopsy instrument according to claim 1, wherein more than one biofunction element is being used with different capture molecules simultaneously.

12. The biopsy instrument according to claim 1, wherein the guide element has a receiver between the distal and proximal portions, which serves to receive the biofunction element.

13. The biopsy instrument according to claim 1, wherein the biofunction element comprises metal, plastic, and/or ceramic materials.

14. The biopsy instrument according to claim 1, wherein the capture molecules are selected the group consisting of antibodies, antibody fragments, peptides, nucleic acids, receptors, inorganic materials or combinations thereof.

15. The biopsy instrument according to claim 1, wherein the spring elastic distal portion of the guide element comprises capture molecules.

16. The biopsy instrument according to claim 1, wherein the biopsy instrument further comprises a covering device.

17. The biopsy instrument according to claim 16, wherein the covering device covers the biofunction element, and wherein the covering device is composed of homopolymers, copolymers, biopolymers, chemically modified polymers and/or synthetic polymers.

18. The biopsy instrument according to claim 1, wherein the biopsy instrument has a longitudinal bore for receiving a mandrain and/or other functional elements.

19. The biopsy instrument according to claim 10, wherein the outer diameter of the biofunction element is 0.01 to 0.1 mm smaller than the outside diameter of the distal portion of the guide element.

20. The biopsy instrument according to claim 5, wherein (i), (ii) and (iii) of the biopsy instrument are configured for insertion into and removal from a body of a patient.

21. The biopsy instrument according to claim 1, wherein the surfaces that come in contact with the biopsy instrument are a vessel wall or an organ.

22. A method of enriching a sample material, comprising providing the biopsy instrument of claim 1, inserting, through a vascular access, and enriching the sample material via said detecting molecules of said biofunction element.

23. The method of claim 22, wherein the sample material is from the vascular system, efferent glandular ducts of the pancreas, lachrymal gland, parotid gland, efferent glandular ducts of the mucosal glands, mixed glands, skin and sweat glands, mammary glands, spinal canal, ventricular system, epidural space, gall bladder and their efferent anatomical structures, efferent urinary tract or the lymphatic system and body cavities of the abdomen, the chest, the uterus, the urogenital apparatus, or a joint, or the gastrointestinal tract.

24. The method of claim 22, wherein the biopsy instrument is placed into the vascular system via an auxiliary endoscopic tool.

25. A method for enriching a sample comprising providing a biopsy instrument according to claim 1, inserting, through a vascular access, the biopsy instrument into a vascular system and enriching the sample material via the detecting molecules of said biofunction element to obtain an enriched sample.

26. The method of claim 25, wherein the biopsy instrument is adapted to detect gene mutations prenatally, chromosome mutations and chromosomal aberrations from the group consisting of deletion, inversion, duplication, translocation, ring chromosomes, and/or a failure of gene transcription, gene translation, mRNA stability, splicing variants, a disorder of mRNA transport into the cytoplasm, protein biosynthesis and/or epigenetic factors.

27. The method of claim 25, wherein the enriched sample is used for cancer diagnosis, primary diagnosis, tumor diagnosis and/or tumor grading.

28. The method of claim 25, wherein the enriched sample is used for monitoring of tumor treatment, monitoring of an autologous, syngeneic, allogeneic, xenogeneic or alloplastic transplant, monitoring of an inflammatory disease, monitoring of infectious disease, monitoring of a hormonal disorder, monitoring of a psychiatric disorder and/or monitoring of a neurodegenerative disease via said sample.

29. The method of claim 25, wherein the enriched sample is used for prenatal diagnosis, cancer diagnosis and the monitoring of a therapy course, as well as diagnosis of a disease selected from the group consisting of inherited diseases, proliferative diseases, inflammatory diseases, autoimmune diseases, infectious diseases, hormonal disorders, diseases of blood and blood-forming organs, diseases of the digestive tract, liver, bile, the pancreas, diseases of the urogenital tract and kidney, diseases of the heart, abnormal changes in blood vessel system and lymphatic system disorders, pulmonary conditions, diseases of the central or peripheral nervous system and the electrical stimulus transmission and/or neurodegenerative diseases.

30. The method of claim 29, wherein the proliferative disease comprises tumors, precancerous growths, dysplasia, and neuroendocrine tumors, endometriosis and/or metaplasia.

31. The method of claim 29, wherein the autoimmune disease is selected from the group consisting of rheumatoid arthritis, inflammatory bowel disease, osteoarthritis, neuropathic pain, alopecia areata, psoriasis, psoriatic arthritis, acute pancreatitis, allograft rejection, allergies, allergic inflammation of the lung, multiple sclerosis, Alzheimer's disease, Crohn's disease and/or systemic lupus erythematous.

32. The method of claim 29, wherein the infectious disease is selected from the group consisting of parasitic diseases, bacterial diseases, and/or viral diseases.

33. The method of claim 29, wherein the hormonal disorder is selected from the group consisting of diseases of glucose metabolism, lipid metabolism, protein metabolism, sexual development and reproduction, water-salt balance, growth, and/or cell formation.

34. The method of claim 29, wherein the hereditary disease is selected from the group including autosomal recessive, autosomal dominant, gonosomal, mitochondrial and/or extra-chromosomal genetic defects and/or disorders that are traced back to a genetic predisposition.

* * * * *

UNITED STATES PATENT AND TRADEMARK OFFICE
CERTIFICATE OF CORRECTION

Page 1 of 1

PATENT NO. : 9,943,292 B2
APPLICATION NO. : 13/058735
DATED : April 17, 2018
INVENTOR(S) : Ulrich Pison et al.

It is certified that error appears in the above-identified patent and that said Letters Patent is hereby corrected as shown below:

On the Title Page

Column 1, Line 1, Inventor (Item (75)), insert --Wolfgang Meissner, Berlin (DE)--

Signed and Sealed this
Nineteenth Day of March, 2019

Andrei Iancu
*Director of the United States Patent and Trademark Office*